United States Patent
Vingerhoets et al.

(10) Patent No.: US 9,841,400 B2
(45) Date of Patent: Dec. 12, 2017

(54) SYSTEM AND METHOD FOR DETECTING SMOLDERING IN PROCESSES WITH CONTINUOUS AIR FLOW

(71) Applicant: Fike Corporation, Blue Springs, MO (US)

(72) Inventors: Jim Vingerhoets, Rijkevorsel (BE); Jan-Bart Seymortier, Onze-Lieve-Vrouw-Waver (BE)

(73) Assignee: Fike Corporation, Blue Springs, MO (US)

( * ) Notice: Subject to any disclaimer, the term of this patent is extended or adjusted under 35 U.S.C. 154(b) by 126 days.

(21) Appl. No.: 14/856,833

(22) Filed: Sep. 17, 2015

(65) Prior Publication Data

US 2017/0082573 A1 Mar. 23, 2017

(51) Int. Cl.
*G01N 27/416* (2006.01)
*G08B 21/12* (2006.01)
*G01N 33/00* (2006.01)
*A61G 10/02* (2006.01)
*G08B 17/117* (2006.01)

(52) U.S. Cl.
CPC ....... *G01N 27/416* (2013.01); *G01N 27/4163* (2013.01); *G01N 33/0063* (2013.01); *G08B 21/12* (2013.01); *A61G 10/026* (2013.01); *G01N 33/004* (2013.01); *G01N 33/007* (2013.01); *G08B 17/117* (2013.01)

(58) Field of Classification Search
CPC ............. G01N 27/416; G01N 27/4163; G01N 33/007; G01N 33/004; G08B 21/12; G08B 17/117; A61G 10/026
See application file for complete search history.

(56) References Cited

U.S. PATENT DOCUMENTS

| | | | |
|---|---|---|---|
| 5,079,930 A * | 1/1992 | Beaverson | F25B 40/02 62/129 |
| 5,691,703 A | 11/1997 | Roby et al. | |
| 8,786,454 B2 | 7/2014 | Siddall | |
| 9,035,243 B2 * | 5/2015 | Lenkeit | G08B 17/11 250/287 |

(Continued)

OTHER PUBLICATIONS

The International Search Report and Written Opinion dated Dec. 8, 2016, in PCT/US2016/051586 in Sep. 14, 2016.

*Primary Examiner* — Mohamed Barakat
(74) *Attorney, Agent, or Firm* — Hovey Williams LLP (57) ABSTRACT

A system (20) and method (100) using decentralized trace gas sensors (44a, 44b, 44c) and a central control element (46) to detect smoldering material in particulate material processing equipment (26) with continuous air flow (22, 24, 34). First and second sensors (44a, 44c) measure gas concentrations at an air inlet (22) and an air outlet (34), respectively. The control element (46) receives the measurements from the sensors (44a, 44c) simultaneously, considers the first and second concentrations simultaneously to determine an amount of gas being produced in the processing equipment (26), determines whether the amount of gas being produced exceeds a threshold value indicative of smoldering, and if so, activates an alarm. A user interface (48) allows a user to interact with the control element (46), including resetting the alarm, viewing current and stored sensor and system information, and initiating a test of the system by exposing the sensors (44a, 44b, 44c) to gas released from a gas reservoir (50a, 50b, 50c).

27 Claims, 4 Drawing Sheets

(56) References Cited

U.S. PATENT DOCUMENTS

| | | |
|---|---|---|
| 9,075,007 B2 | 7/2015 | McKendree |
| 2012/0058013 A1* | 3/2012 | Swanson ............ B01D 53/8625 |
| | | 422/109 |
| 2014/0156090 A1* | 6/2014 | Krishnan ............. G05D 7/0617 |
| | | 700/282 |
| 2014/0203942 A1 | 7/2014 | Warmack et al. |
| 2015/0165249 A1* | 6/2015 | Matchett .................. A62C 3/04 |
| | | 169/45 |

* cited by examiner

SYSTEM AND METHOD FOR DETECTING SMOLDERING IN PROCESSES WITH CONTINUOUS AIR FLOW

BACKGROUND OF THE INVENTION

Field of the Invention

The present invention is broadly concerned with detecting smoldering fires in processing equipment with continuous air flow. More particularly, the present invention is concerned with using decentralized carbon monoxide or other trace gas detectors and centralized signal processing to detect smoldering fires in spray dryers, dust collectors, mills, and other processing equipment that operate with continuous air flow.

Description of the Prior Art

In spray dryers, a liquid or slurry of a product is atomized to small droplets and then dried by sudden contact with hot air to powder particles having particular particle sizes. Spray dryers can be found in the food and diary industries, where they are used, for example, in the production of milk powder, cacao, and coffee powder, and also in the pharmaceutical and chemical industries. Slow exothermic reactions of powder deposits in hot regions of drying chambers may evolve over a critical residence period into smoldering fires, which may ultimately result in open flames and/or dust explosions. The likelihood of such events can be reduced by controlling drying temperatures and following thorough cleaning practices.

One way to detect and prevent smoldering fires involves monitoring exhaust air temperature. This solution suffers from several problems and limitations, including that, as a result of high air flow through the drying system, high heat associated with large fires already in progress is required before such systems detect and attempt to extinguish the fires (by, e.g., activating a sprinkler system). Another way involves monitoring carbon monoxide (CO) concentrations in an attempt to detect smoldering fires before open flames or explosions occur. More specifically, the smoldering phenomenon is a slow, flameless combustion that emits CO gas, carbon dioxide ($CO_2$) gas, water ($H_2O$) vapor, and heat. Because $CO_2$ and $H_2O$ are more abundantly present in normal air, CO is the most distinctive reaction product. Moreover, some solid organic substances of the smoldering powder are decomposed and evaporated due to the heating, and trace gases other than CO are emitted. Current smolder detection systems are based on CO measurement and use sensitive but expensive infra-red or laser gas analyzers. Because of the high cost of such analyzers, multiple sample points are typically connected to a single centralized sensor which analyzes the samples sequentially. This solution also suffers from several problems and limitations, including long and vulnerable gas sampling lines, delays in detection, and difficulty with filtering stray gases that enter the system from the outside, so that, in practice, the full sensitivity of such sensors is unrealized. For example, fast gas analyzers may have a measurement cycle of approximately fifteen seconds, so if three air streams are sequentially monitored, the smoldering alarm may be delayed by up to forty-five seconds.

A similar risk of smoldering fires arises in other processing equipment involving powdered material and heat. For example, mills break solid materials into smaller pieces by grinding, crushing, or cutting. Similar risks of fires or explosions can arise in mills due to the heat of mechanical friction or impacts, which may be exacerbated by hot air streams, which can cause deposits to begin smoldering.

Dust collectors, which are often used downstream of dryers and mills to separate dust particles from the exhaust air stream, are also exposed to smoldering risk. The risk is created by glowing embers produced by the upstream dryer or mill, transported pneumatically to the dust collector, and which settle into and ignite the collected dust in the hopper of the dust collector.

SUMMARY OF THE INVENTION

The present invention overcomes the problems outlined above and provides a system and method using decentralized CO or other trace gas sensors and a central control element configured to simultaneously receive and process data signals from the sensors to detect smoldering in processing equipment with continuous air flow in which powdered materials may be exposed to sufficient heat to result in smoldering fires.

In one embodiment, the present invention may be characterized as a system broadly comprising a plurality of sensors, an electronic control element, and a user interface. The plurality of sensors may be configured to measure concentrations of a trace gas, and may include a first sensor configured to measure a first concentration of the trace gas at an air inlet, and a second sensor configured to measure a second concentration of the trace gas at an air outlet. The control element may be configured to receive the measurements of the trace gas simultaneously from the plurality of sensors, consider the first concentration of the trace gas and the second concentration of the trace gas simultaneously to determine an amount of the trace gas being produced in the processing equipment, determine whether the amount of the trace gas being produced in the processing equipment exceeds a threshold value indicative of smoldering, and activate an alarm if the amount of the trace gas being produced in the processing equipment exceeds the threshold value. The user interface may be configured to allow a user to interact with the control element, including resetting the alarm.

Various implementations of this embodiment may include any one or more of the following features. The material may be selected from among foods, coals, chemicals, and pharmaceuticals. The processing equipment may be a dryer selected from among spray dryers, ring dryers, and flash dryers and configured to dry a slurry form of the material to produce a powder form of the material. The processing equipment may be a fluid bed dryer located downstream of a spray dryer and configured to further dry a powdered material until a desired humidity is reached. The processing equipment may be a mill selected from among hammer mills, roller mills, and cutter mills and configured to break larger pieces of a material into smaller pieces of the material. The processing equipment may be a dust collector selected from among cyclones, fabric filters, and electrostatic precipitators, and configured to separate dust particles from an air stream originating from other processing equipment such as dryers and mills. The trace gas may be CO and the plurality of sensors may be electro-chemical sensors, or the trace gas may be something other than CO and the sensors may be semiconductor sensors.

When considering the first and second concentrations of the trace gas to determine the amount of the trace gas being produced in the processing equipment, the control element may take into account a delay, a dilution, and/or a time spread of any of the trace gas moving through the processing equipment between the first sensor and the second sensor. The system may be further configured to differentiate between slow variations of the first and second concentrations of the trace gas due to sensor drift and rapid variations of the first and second concentrations of the trace gas due to smoldering.

The system may further include a second air inlet and a third sensor configured to measure a third concentration of the trace gas at the second air inlet, and the control element may be further configured to consider the third concentration of the trace gas and the second concentration of the trace gas to determine a second amount of the trace gas being product in the processing equipment, determine whether the second amount of the trace gas being produced in the processing equipment exceeds the threshold value indicative of smoldering, and activate the alarm if the second amount of the trace gas being produced in the processing equipment exceeds the threshold value.

In determining whether the amount of the trace gas being produced in the processing equipment exceeds the threshold value indicative of smoldering, the control element may consider an equipment profile for the processing equipment, wherein the equipment profile may relate the trace gas concentration to a plurality of different air flow rates for the processing equipment. In determining whether the amount of the trace gas being produced in the processing equipment exceeds the threshold value indicative of smoldering, the control element may consider a smoldering profile for the material, wherein the smoldering profile relates the trace gas concentration to time and temperature for the material.

There may be a plurality of threshold values, and each threshold value may be associated with a particular alarm level, and the control element may be further configured to activate the particular alarm level associated with the threshold value that has been exceeded. The control element may be further configured to determine a rate of change of the concentration of the trace gas being produced in the processing equipment. The user interface may be further configured to allow the user to view current and past measurements of carbon monoxide, and to view information associated with the control element activating the alarm. The system may further include a memory element accessible by the control element and configured to store the measurements of the trace gas from the plurality of sensors, and to store information associated with the control element activating the alarm. The system may further include a gas bottle or other reservoir of the trace gas and a valve, and the control element may be configured to test the system by opening the valve and releasing the trace gas from the reservoir into the system at or near the sensors for measurement by the sensors.

DETAILED DESCRIPTION OF THE PREFERRED EMBODIMENTS

Broadly characterized, the present invention provides a system and method using decentralized CO or other trace gas sensors and a central control element configured to simultaneously process data signals received from the sensors to detect smoldering in processing equipment with continuous air flow in which powdered materials may be exposed to sufficient heat to result in smoldering fires. Such processing equipment may include dryers (e.g., spray, ring, flash or fluid bed dryers), dust collectors (e.g., cyclones, fabric filters, electrostatic precipitators), or mills (e.g., hammer, roller, or cutter mills) used for processing foods (e.g., milk powder), coals, chemicals, or pharmaceuticals.

Figure 1:
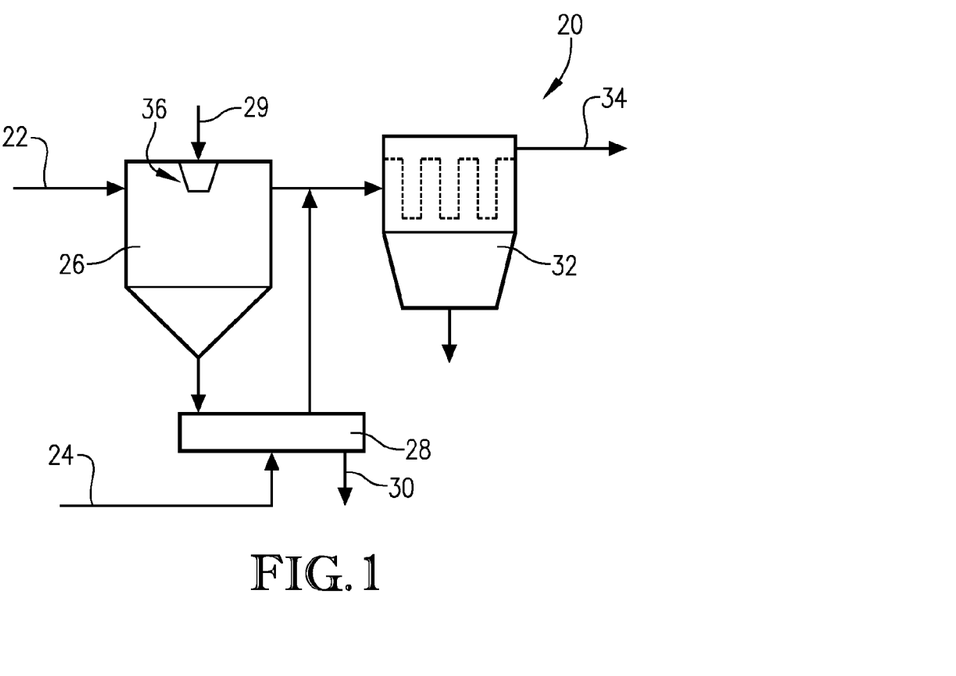
FIG. 1 is a schematic of an exemplary two-stage spray dryer system.

Referring to FIG. 1, an exemplary two-stage spray dryer system 20 configured to dry a liquid or slurry form of a product to produce a dry powdered form of the product may include first and second air inlets 22, 24, a drying chamber 26, a fluid bed 28, a product inlet 29, a product outlet 30, a dust collector 32, and an exhaust outlet 34. It will be appreciated that this and other processing systems may include substantially any number of additional inlets and/or outlets. Heated air may enter the system 20 through the first and second air inlets 22, 24. The first air inlet 22 may be connected to and deliver the heated air to the drying chamber 26. The second air inlet 24 may be connected to and deliver the heated air to the fluid bed 28. An initial stage of drying may occur in the drying chamber 26. In particular, the liquid or slurry form of the product may be introduced into the drying chamber 26 through product inlet 29 and directed toward a rotary atomizer or high pressure nozzle 36 which atomizes the liquid or slurry. When the resulting extremely small droplets of liquid or slurry are contacting by the stream of heated air at least some of the moisture inside the droplets may evaporate. A second stage of drying may occur in the fluid bed 28. Inside the fluid bed 28, the heated air may be distributed through perforated plates on which the partially dried powder particles rest. The velocity of the heated air may cause the powder particles to become airborne to the extent that only the finest and smallest particles leave the fluid bed 28 with the air, while the larger particles are transported with the upward and forward directed flow of heated air through the product outlet 30. The dry powdered product may exit the fluid bed 28 through the outlet 30 toward a storage silo or bag-filling station. The heated air and the fine particles suspended in it may be filtered through the dust collector 32 and then vented to the atmosphere via the exhaust outlet 34.

Figure 2:
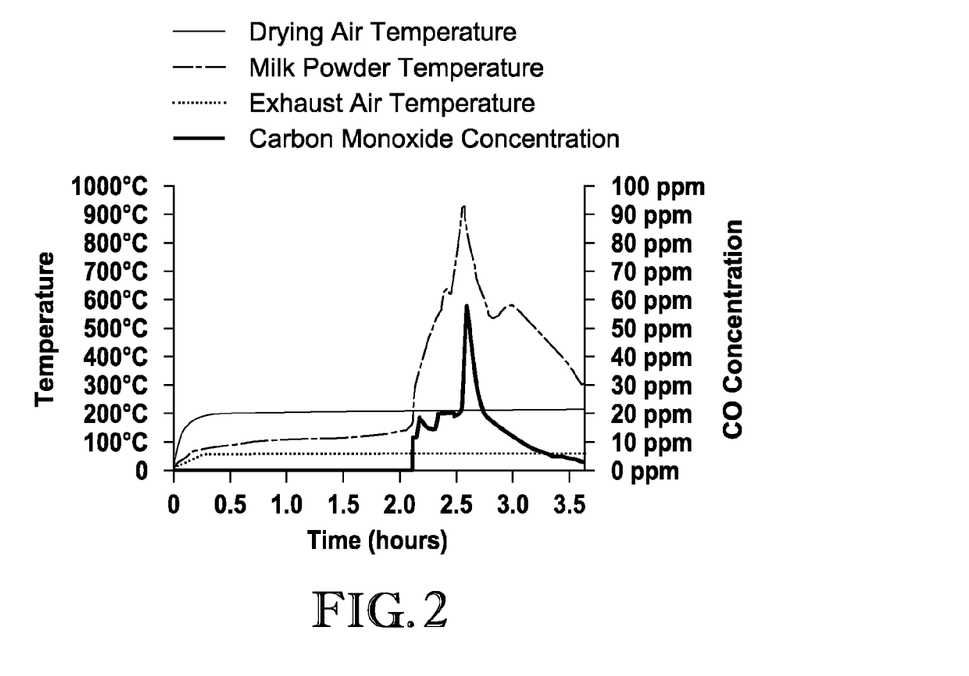
FIG. 2 is a graph of time versus temperature for milk powder undergoing self-ignition during overheating such as might occur in the exemplary two-stage spray dryer system of FIG. 1, wherein the graph includes CO concentrations associated with smoldering evolving into self-ignition.

In an experiment, 220 grams of milk powder were positioned for several hours in the 200° C. hot air stream of such a spray drier having a drying air flow rate of approximately 3500 kg/h. FIG. 2 is a graph of the temperature of the powder versus the concentration of CO in the exhaust air. After approximately 2 hours, the powder began smoldering and reached 900° C. without exhibiting open flames. Simultaneous with auto-ignition, a sudden increase in CO concentration was measured to a peak value of approximately 55 ppm. Importantly, the exhaust air temperature did not increase. Thus, it was concluded that the concentration of CO was a more reliable indicator of smoldering than temperature.

Figure 3:
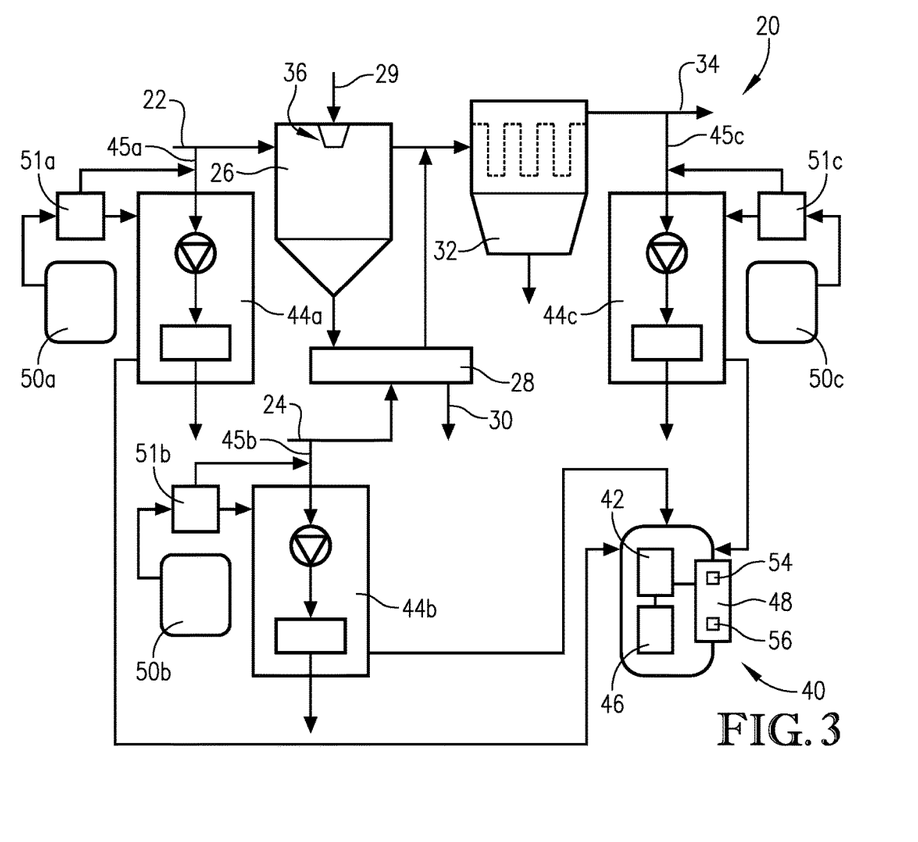
FIG. 3 is a schematic of an embodiment of a smolder detection system installed in the exemplary two-stage spray dryer system of FIG. 1.

Several issues may influence the design of a system to detect smoldering based on CO. One issue is that the concentration of CO in the spray dryer depends on both the size and growth rate of the smoldering combustion, as well as the amount of air throughput. Drying systems operate with large quantities of drying air, and the amount of CO generated by a smoldering deposit may be diluted to low concentration levels. For example, in the experiment reflected in FIG. 2, if the amount of drying air were increased to 190,000 kg/h, the peak amount of CO would be decreased to only 1 ppm.

Another issue is that spurious detection of CO from external sources such as combustion gases from burners or engine exhausts could lead to false alarms. One way to avoid such spurious detection and resulting false alarms to is to apply differential measurement. Both the drying air as well as the exhaust air may be monitored, and the system may trip upon reaching a threshold difference in gas concentration. Variations in gas concentration may appear delayed, diluted, and/or spread over time in the exhaust air due to the influences of the air flow and geometry of the processing equipment. As a result of such time-shifting and spreading, direct differential measurement may lead to false alarms. Thus, it may be desirable to use more sophisticated differential measurement which takes into account such factors as delay, dilution, and time spread.

In one implementation, tests may be performed to determine the values and any changes in those values over time of relevant variables (e.g., air flow rates, spurious air flow ingress and egress leakage rates, spurious trace gas ingress rates) associated with specific processing equipment. Additionally or alternatively, tests may be performed to determine the amount of CO generated by the smoldering of specific products under specific conditions. In particular, small amounts of different products may be exposed to different temperatures, air flow rates, and/or other conditions until brought to self-ignition. During such tests, the temperatures of the product samples as well as the CO concentrations in the exhaust air may be monitored to create a plurality of baseline smoldering profiles.

More specifically, smoldering in a spray drier may produce CO gradually, from an initially slow rate (in terms of hours) to a rapidly increasing rate (in terms of minutes) once open flames appear, and fires may be preceded by large CO concentrations. Table 1 provides results of testing on skim milk powder and shows the amount of CO that was generated for three random smoldering sizes at two representative smoldering temperatures and three representative exhaust air flows. Linear scaling rules were applied for smoldering size and exhaust air flow. At a smoldering temperature of 600° C., no open flames were generated and there was no immediate risk of rapid expansion or dust explosion. However, as the smoldering temperature increased to 1200° C., open flames appeared and the risk of imminent rapid fire expansion or dust explosion can be assumed.

TABLE 1

Amount of CO generated by skim milk powder for various smoldering sizes and temperatures for spray dryer sizes

| Exhaust air flow | Typical liquid milk capacity* | 200 g | | 500 g | | 1500 g | |
|---|---|---|---|---|---|---|---|
| | | 600° C. | 1200° C. | 600° C. | 1200° C. | 600° C. | 1200° C. |
| 20000 kg/h | 2000 kg/h | 2.3 ppm | 14 ppm | 5.7 ppm | 35 ppm | 17 ppm | 103 ppm |
| 100000 kg/h | 10000 kg/h | 0.5 ppm | 2.8 ppm | 1.1 ppm | 6.9 ppm | 3.4 ppm | 21 ppm |
| 400000 kg/hr | 40000 kg/hr | 0.1 ppm | 0.7 ppm | 0.3 ppm | 1.7 ppm | 0.9 ppm | 5.2 ppm |

*based on 7% water content in exhaust air and 70% water content in liquid milk.

Referring to FIG. 3, in an embodiment of the present invention, a smolder detection system 40 may broadly comprise a memory element 42, a plurality of electro-chemical CO sensors 44*a*, 44*b*, 44*c*, an electronic control element 46, and an interface element 48. It will be appreciated that the system 40 may include substantially any number of additional sensors. The smoldering detection system 40 may be installed in the exemplary two-stage spray dryer system 20 of FIG. 1 or in other processing equipment in which smoldering may be a concern.

The memory element 42 may be wiredly or wirelessly connected to the control element 46 and configured to store information which may be useful to the control element 46 in detecting smoldering fires. In one implementation, processing equipment profiles and smoldering profiles may be pre-determined experimentally to, e.g., identify appropriate alarm levels and determine residual risks not covered by the system 40, and then the alarm level thresholds and any other useful information may be stored in the memory element 42 for subsequent use by the installed system 40. Additionally or alternatively, the memory element 42 may store one or more processing equipment profiles reflecting relevant variables (e.g., air flow rates, spurious air flow ingress and egress leakage rates, spurious trace gas ingress rates) associated with particular processing equipment, and/or on or more smoldering profiles reflecting the measured CO concentrations, and possible other relevant variables, associated with particular materials under particular processing conditions (e.g., temperatures, air flow rates), and then the triggering of the alarm by the system 40 is based on the combination of the measured CO concentration and additional process related information. The memory element 42 may log and store at a periodic rate (e.g., once per second) such information as raw sensor data, drift compensated gas concentration data, and total calculated process gas concentration data. The memory element 42 may further log and store system events whenever they occur, including the date and time and a description of the event. Such system events may include the occurrence of status condition events; the setting and resetting of variables associated with Alarm, Trouble, Supervisory, Disable, and System Test variables (which are described below); the setting and resetting of interlocks; any user commands initiated via the Interface; the results of system tests (e.g., failed or passed, time of system test start and system test end, system test configuration values); and the actual daily values of all system configuration variables.

The plurality of electro-chemical CO sensors 44*a*, 44*b*, 44*c* may be wiredly or wirelessly connected to the control element 46 and configured to measure CO concentrations at various points in the processing equipment and to report those measured CO concentrations to the control element 46 for use in detecting smoldering fires. One or more of the sensors 44a, 44b, 44c may be positioned at the first and/or second air inlets 22,24 to measure the concentration of CO entering the system 20, which can then be treated as noise when examining the concentrations of CO detected further into the system 20.

In one implementation, some or all of the sensors 44a, 44b, 44c may be additionally or alternatively configured to measure and report concentrations of other trace gases, that is, any gas that makes up less than 1% by volume of the Earth's atmosphere. These trace gas sensors may be so-called "semiconductor" sensors which employ a metal oxide semiconductor and of which the electrical resistance of the heated sensing layer changes when brought into contact with small concentrations of trace gases, amongst which a variety of volatile organic compounds.

Figure 4:
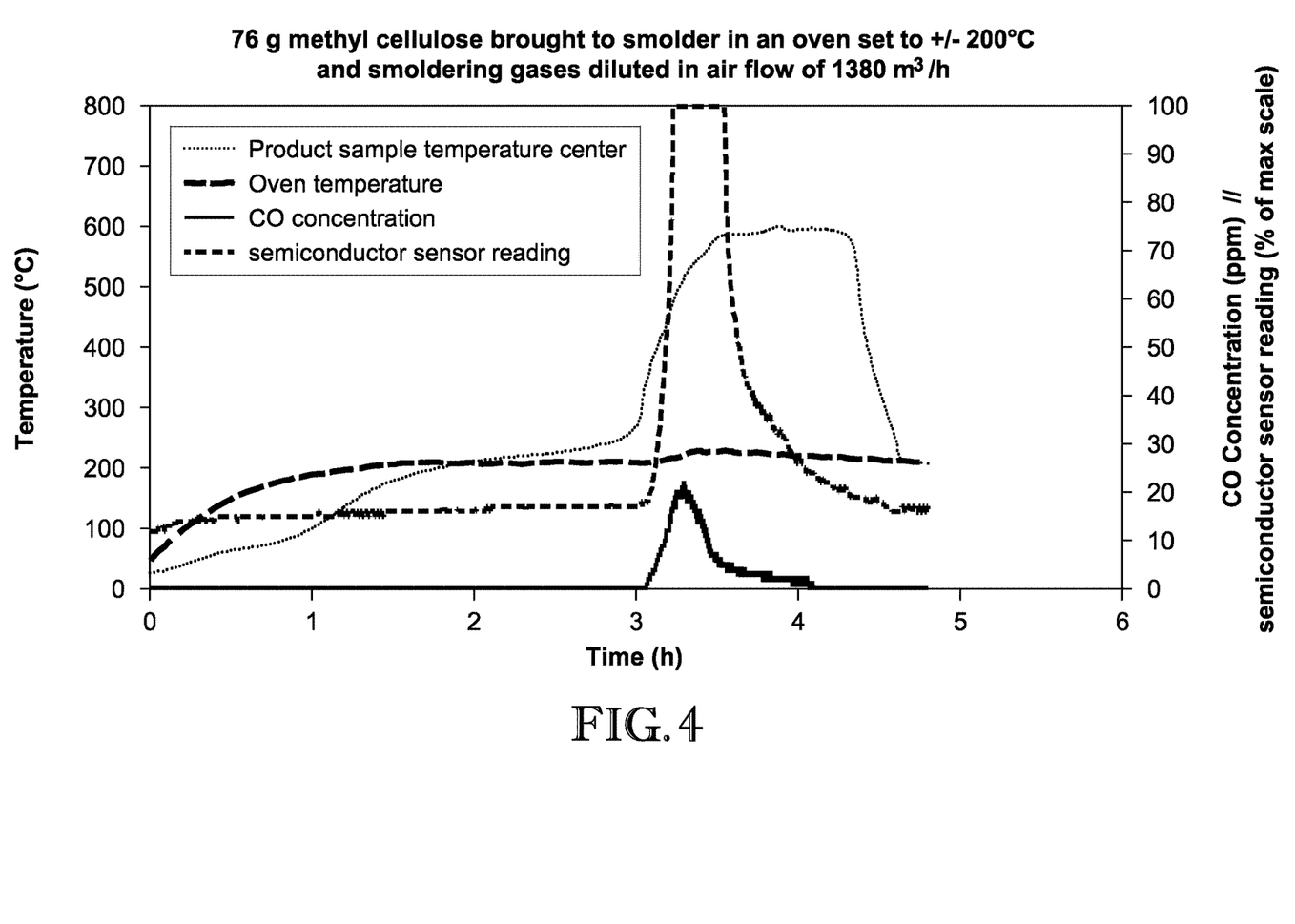
FIG. 4 is graph of time versus temperature for methyl cellulose undergoing self-ignition during overheating such as might occur in a cutter milling system, wherein the graph includes CO and trace gas concentrations associated with smoldering evolving into self-ignition.

The trace gas sensors may be configured to narrowly detect one or a few specific trace gasses or to broadly detect a larger number of different trace gases. Referring to FIG. 4, in a demonstrative experiment, 76 g of methyl cellulose powder was brought to self-ignition in an oven set to approximately 200° C. After smoldering started, the powder temperature rose to approximately 600° C. The oven was ventilated and the ventilation gases were diluted in an air stream of approximately 1380 m3/hour. Both an electro-chemical carbon monoxide sensor and a broad-spectrum semiconductor trace gas sensor installed in the air stream signaled the occurrence of smoldering.

Each sensor 44a, 44b, 44c may be connected to a point in the processing equipment by relatively short sample air extraction lines 45a, 45b, 45c. In one implementation, each sensor cell may include a housing, two electrodes, connecting wires, and an electrolyte. CO is oxidized at one electrode to $CO_2$ while oxygen is consumed at the other electrode. The electrical current between the electrodes is proportional to the concentration of CO. Pollutants in the process air, such as dust and water vapor, may not interfere or significantly interfere with the measurements, but it may be advisable to regularly re-calibrate the sensor and to replace the sensor at periodic intervals (e.g., every two to five years) to maintain accuracy and reliability. The relatively low cost of such electro-chemical CO sensors allows for using individual sensors for each process air stream, rather than using a central gas analyzer with sample air transportation lines. The use of a plurality of sensors provides advantages over traditional centralized infrared gas analyzers to detect smoldering deposits in spray driers. In particular, they allow for shorter gas sampling lines and provide faster responses, easier installation and maintenance, lower cost of ownership, lower sensitivity to stray CO entering the spray dryer, and lower sensitivity to water vapor in the process air, all of which results in a simpler, faster, less expensive, and more reliable solution.

The control element 46 may be wiredly or wirelessly connected to the memory element 42 and to the plurality of CO sensors 44a, 44b, 44c and configured to use information stored in the memory element 42 and received from the plurality of sensors 44a, 44b, 44c to determine whether smoldering is occurring, and if it is, to take one more actions. In one implementation, this may be accomplished by comparing sensor measurements of actual CO concentrations with stored CO concentration alarm levels. The sensors 44a, 44b, 44c and control element 46 may sample the airflow once each second and round the measured CO concentrations to 1% and 0.1 ppm accuracy. CO produced by smoldering may be diluted but still detectable in the process air. In one implementation, the control element 46 may power the sensors 44a, 44b, 44c and read the measured CO and trace gas concentration values from the sensors 44a, 44b, 44c as follows: 4 mA=0.0 ppm CO, minimum detection value; 20 mA=50.0 ppm CO, maximum detection value. Values between 0 and 4 mA may be used for transmitting trouble, warning, or maintenance statuses. The sensors' 44a, 44b, 44c baseline signal may be calibrated to a value approximately between 12% and 18%, or approximately 15%, of the maximum detection value, which represents the concentration of trace gases in local ambient air.

In an exemplary scenario, an embodiment of the system 40 may function substantially as follows. The control element 46 may determine that the Pre-Alarm threshold of 0.8 ppm of CO has been reached, and may communicate a notification to that effect. Subsequently, the control element 46 may determine that the Alarm1 threshold of 2 ppm of CO has been reached, and may communicate an alarm to that effect. Subsequently, the control element 46 may determine that the Alarm2 threshold of 5 ppm of CO has been reached, and may communicate an alarm to that effect and take action to prevent a fire or explosion, wherein such action may include shutting down the process and/or activating a sprinkler or other fire-suppression system.

In addition to calculating the static concentration values of gases produced inside the process, the control element 46 may also calculate once each second the mean rates with which the process gas concentrations rose over a time period (e.g., the last 10 seconds). This may be accomplished by subtracting the current gas concentrations from the gas concentrations of 10 seconds earlier and by dividing the differences by 10 seconds to arrive at the rate of change. Very slow and persistent changes in sensor readings may be interpreted as zero drift, rather than as the presence of smoldering gas. In order to filter out slow sensor zero drift from the measurement system and prevent false alarms, an average value of the sensor over a longer period of time may be subtracted from the actual sensor reading before assessing the alarm levels.

To avoid spurious gases entering the process and falsely tripping the detection system, the control element 46 may utilize differential measurement in which both the inlet air as well as the outlet air is monitored and the difference in gas concentration levels is used to trip the detection system. Direct differential measurement may still lead to false alarms due to time shifting and spreading. The present invention may employ differential measurement that takes into account that gas concentration variations in the inlet air may appear delayed, diluted, and/or spread over time at the exhaust air, where the delay and the rate of dilution and time spreading may depend on air flows and the geometry of the processing equipment 20.

For example, the effects of delay, dilution, and time spreading for a system with one air inlet and one air outlet may be predicted using a first order model of the format:

$$C_{outlet}(t) = C_{outlet}(t-1).X + C_{inlet}(t-\Delta t).Y$$

wherein,
t is an integer number indicating the processing timestamp;
$C_{inlet}$ is the concentration of CO or other trace gases entering the process at the air inlet;
$C_{outlet}$ is the concentration of CO or other trace gases that appears at the air outlet assuming no extra gases are generated inside the process;
$\Delta t$ is a measure of the delay time (i.e., the time to transport gasses from the air inlet to the air outlet);
the sum X+Y (<1) is a measure of the dilution, wherein the lower the sum X+Y, the more dilution is modelled, and if the sum X+Y=1, then no dilution is modelled;

ratio X/Y is a measure of the time spreading, wherein the higher ratio X/Y the more time spreading is modelled; and if coefficient X=0, then coefficient Y equals the ratio of process flow at air inlet and air outlet $Q_{inlet}/Q_{outlet}$.

Relatedly, the system may be further configured to differentiate between slow variations of the first and second concentrations of CO due to sensor drift and rapid variations of the first and second concentrations of CO due to smoldering.

In one implementation, the control element 46 may include digital electronic output interlocks and digital electronic input interlocks. All interlocks may be failsafe and redundant, and the unpowered status of the interlocks may be the safe status. The output interlocks may represent the system status and may be used by the process control system to control the likelihood of fire or explosion due to smoldering. The output interlocks may include Alarm, Trouble, and Supervisory interlocks. The Alarm interlocks may be switched on if the concentration of gas generated inside the process exceeds programmed alarm levels stored in the memory element 42. In particular, the PreAlarm interlock may indicate that the output gas concentration has exceeded a predetermined threshold level. The Alarm1 interlock may indicate that the output gas concentration has exceeded a second predetermined intermediate level. The Alarm2 interlock may indicate that the output gas concentration has exceeded a third predetermined maximum level.

The latching alarms may further include two latching status variables which indicate that an unexpected internal failure has occurred. In particular, the Trouble status may indicate a low priority failure without a loss of safety function, while the Supervisory status may indicate a high priority failure with a loss of safety function. The Trouble status may be switched on under any of the following conditions: Positive or negative trace gas sensor drift or positive or negative CO sensor drift. The Supervisory status may be switched on under any of the following conditions: Sensor fault, sensor maintenance signal, sensor calibration signal, system test failure, or control element error signal.

The input interlocks may include SystemTest, RemoteDisable, and LocalDisable interlocks. The SystemTest input interlock may be configured to allow for initiating a test of the system. In order to execute the test of the system, the control element 46 may switch on gas injection valves to introduce a trace gas into gas sampling lines and verify that the appropriate gas concentrations are measured by the sensors. The RemoteDisable input interlock may be configured to allow for setting the system in a Disable status. The Disable function may allow for performing maintenance on the processing equipment or on the smoldering detection system itself without risking setting the Alarm, Trouble, or Supervisory Interlocks and without having to cut power to the system. The LocalDisable interlock may also be configured to allow for setting the system in the Disable status, but may be connected to a local Disable key switch of the control element itself.

With regard to testing the system 40, the control element 46 may be configured to enact a test procedure involving the functional testing of the correct sampling and detection of all sensors 44a, 44b, 44c and the correct reading of gas sensor measurements by the control element 46. In one implementation, all of the sensors 44a, 44b, 44c may be connected to one or more test gas bottles 50 and solenoid valves 51a, 51b, 51c which allow for introducing test gases, such as CO and trace gases (e.g., butane), from the bottles 50a, 50b, 50c into the gas sampling lines 45a, 45b, 45c. After initiation of a test of the system 40, the control element 47 may open the test gas valves 51a, 51b, 51c for certain durations and determine whether the gas measurements of each sensor 44a, 44b, 44c reaches a threshold concentration within a certain amount of time. If one or more of the sensors 44a, 44b, 44c does not reach the expected threshold concentration and drop back under that threshold and also under the lowest active alarm level within a predetermined time period, then the test may be deemed a failure.

The user interface 48 may be wiredly or wirelessly connected to the control element 46 and configured to visually and/or audibly or otherwise communicate to a user such information as current sensor readings, short-term prior sensor readings (over, e.g., the prior 30 minute period), long-term prior sensor readings (over, e.g., the prior day or week), and event listings and descriptions. The user interface 48 may be further configured to allow the user to perform such actions as confirm a latching Alarm, Trouble, or Supervisory status; initiate a system test; abort a system test; set or reset an interlock, set or reset drift compensation (after, e.g., sensor calibration or replacement).

In one implementation, safety-related user actions via the user interface 48 may require a hardwired acknowledgement procedure to avoid accidentally changes to system settings. In one implementation of this acknowledgement procedure, a user's attempt to enter a safety-related command or request a change to a safety-related system parameter may result in the control element 46 activating a hard-wired acknowledgement LED 54, indicating that the user must confirm the command or change to the parameter. The user may push a hard-wired acknowledgment button 56 to do so, and the control element 46 may then deactivate the LED 54 and process the command or change to the parameter. The control element 46 may inform the user via the user interface when the command or change to the parameter has been successfully completed.

Figure 5:
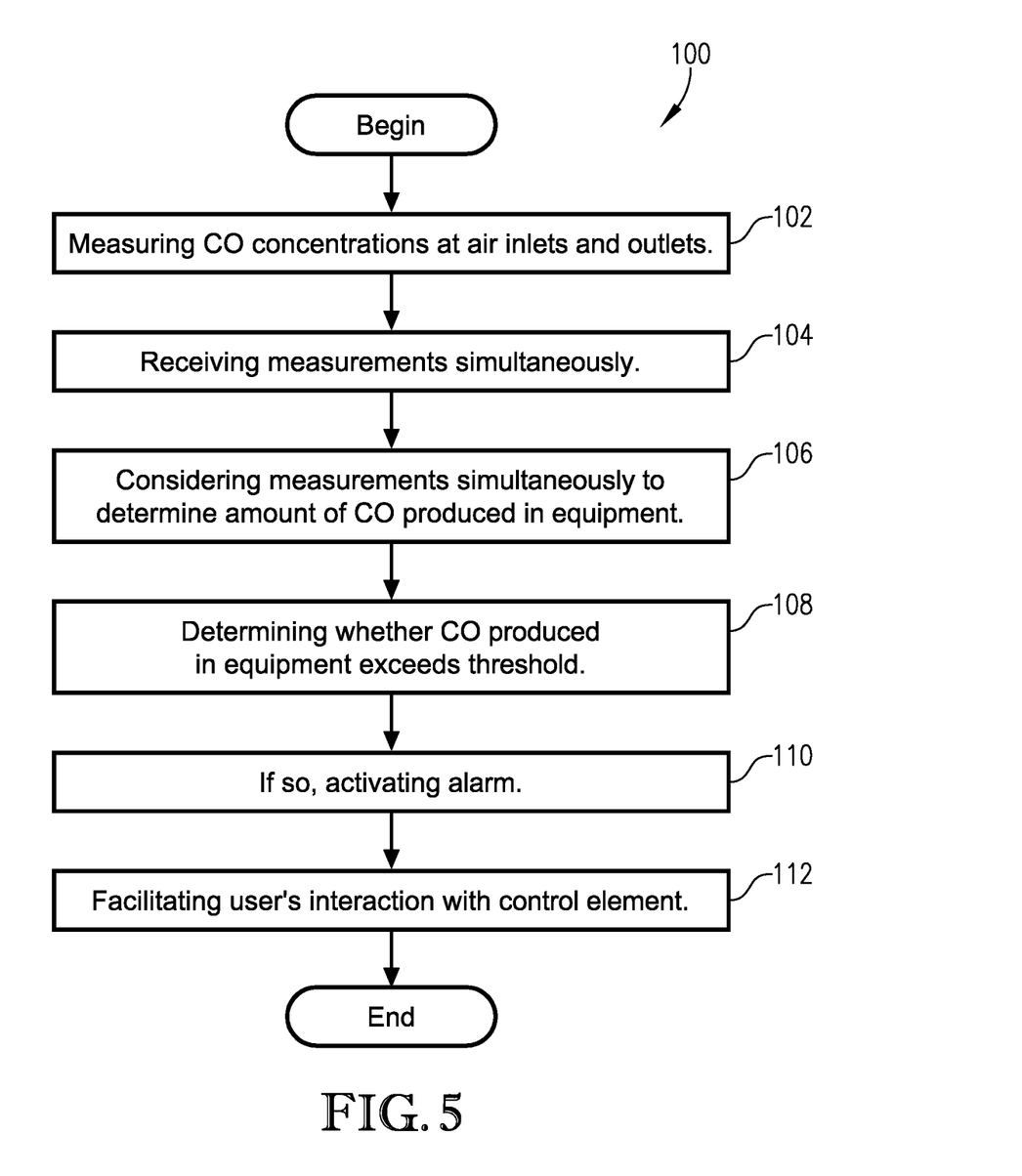
FIG. 5 is a high-level flowchart of steps involved in the functioning of the smolder detection system of FIG. 4.

Referring to FIG. 5, characterized as a method 100 for detecting the smoldering of a material in processing equipment 20, the present invention may broadly function as follows. The plurality of electro-chemical sensors 44a, 44b, 44c may measure concentrations of CO, as shown in step 102, including measuring a first concentration of CO at the air inlet 22, and measuring a second concentration of CO at the air outlet 24. The control element 46 may receive the measurements of CO simultaneously from the plurality of electro-chemical CO sensors 44a, 44b, 44c, as shown in step 104. The control element 46 may consider the first concentration of CO and the second concentration of CO simultaneously to determine an amount of CO being produced in the processing equipment 20, as shown in step 106, which may include taking into account such factors as a delay, a dilution, and a time spread of any CO moving through the processing equipment 20 between the air inlet 22 and the air outlet 24. The control element 46 may determine whether the amount of CO being produced in the processing equipment 20 exceeds a threshold value indicative of smoldering, as shown in step 108. The control element 46 may activate an alarm if the amount of CO being produced in the processing equipment 20 exceeds the threshold value, as shown in step 110. The user interface 48 may facilitate a user interacting with the control element 46, as shown in step 112, which may include allowing the user to perform such actions as resetting the alarm, viewing current and past measurements of carbon monoxide, and viewing information associated with the control element activating the alarm.

Thus, it will be appreciated that embodiments and implementations of the present invention provide advantages over prior art solutions, including that the sensors monitor their air streams and report measurements to the control element simultaneously, and the control element considers those measurements simultaneously. Thus, the reaction time of control element in detecting smoldering may be significantly shorter than other systems which must switch sequentially between air streams and results.

Although the invention has been described with reference to the one or more embodiments illustrated in the figures, it is understood that equivalents may be employed and substitutions made herein without departing from the scope of the invention as recited in the claims.

We claim:

1. A system for detecting a smoldering of a material in a processing equipment, the processing equipment having a first air inlet and an air outlet, the system comprising:
   a plurality of sensors configured to measure concentrations of a trace gas, including a first sensor configured to measure a first concentration of the trace gas at the first air inlet, and a second sensor configured to measure a second concentration of the trace gas at the air outlet;
   an electronic control element configured to receive the measurements of the trace gas simultaneously from the plurality of sensors, consider the first concentration of the trace gas and the second concentration of the trace gas simultaneously to determine an amount of the trace gas being produced in the processing equipment, wherein in considering the first and second concentrations of the trace gas simultaneously to determine the amount of the trace gas being produced in the processing equipment, the electronic control element takes into account a delay, a dilution, and a time spread of any of the trace gas moving through the processing equipment between the first sensor and the second sensor, determine whether the amount of the trace gas being produced in the processing equipment exceeds a threshold value indicative of smoldering, and activate an alarm if the amount of the trace gas being produced in the processing equipment exceeds the threshold value; and
   a user interface configured to allow a user to interact with the electronic control element, including resetting the alarm.

2. The system as set forth in claim 1, wherein the material is selected from the group consisting of foods, coals, chemicals, and pharmaceuticals.

3. The system as set forth in claim 1, wherein the processing equipment includes a dryer selected from the group consisting of spray dryers, ring dryers, and flash dryers, and wherein the dryer is configured to dry a slurry form of a material to produce a powder form of the material.

4. The system as set forth in claim 1, wherein the processing equipment includes a fluid bed dryer located downstream of a spray dryer and configured to further dry a powdered material until a desired humidity is reached.

5. The system as set forth in claim 1, wherein the processing equipment includes a mill selected from the group consisting of hammer mills, roller mills, and cutter mills and configured to break larger pieces of a material into smaller pieces of the material.

6. The system as set forth in claim 1, wherein the processing equipment includes a dust collector selected from the group consisting of cyclones, fabric filters, and electrostatic precipitators, and configured to separate dust particles from an air stream originating from other processing equipment such as dryers and mills.

7. The system as set forth in claim 1, wherein the trace gas is carbon monoxide and the plurality of sensors are electrochemical sensors.

8. The system as set forth in claim 1, wherein the plurality of sensors are semiconductor sensors.

9. The system as set forth in claim 1, wherein the system is further configured to differentiate between slow variations of the first and second concentrations of the trace gas due to sensor drift and rapid variations of the first and second concentrations of the trace gas due to smoldering.

10. The system as set forth in claim 1, further including a second air inlet and a third sensor configured to measure a third concentration of the trace gas at the second air inlet, and wherein the electronic control element is further configured to consider the third concentration of the trace gas and the second concentration of the trace gas simultaneously to determine a second amount of the trace gas being produced in the processing equipment, determine whether the second amount of the trace gas being produced in the processing equipment exceeds the threshold value indicative of smoldering, and activate the alarm if the second amount of the trace gas being produced in the processing equipment exceeds the threshold value.

11. The system as set forth in claim 1, wherein in determining whether the amount of the trace gas being produced in the processing equipment exceeds the threshold value indicative of smoldering, the electronic control element considers an equipment profile for the processing equipment, wherein the equipment profile relates the trace gas concentration to a plurality of different air flow rates for the processing equipment.

12. The system as set forth in claim 1, wherein in determining whether the amount of the trace gas being produced in the processing equipment exceeds the threshold value indicative of smoldering, the electronic control element considers a smoldering profile for the material, wherein the smoldering profile relates trace gas concentration to time and temperature for the material.

13. The system as set forth in claim 1, wherein there are a plurality of threshold values, and each threshold value is associated with a particular alarm level, and the electronic control element is further configured to activate the particular alarm level associated with the threshold value that has been exceeded.

14. The system as set forth in claim 1, wherein the electronic control element is further configured to determine a rate of change of the concentration of the trace gas being produced in the processing equipment.

15. The system as set forth in claim 1, wherein the user interface is further configured to allow the user to view current and past measurements of the trace gas, and to view information associated with the electronic control element activating the alarm.

16. The system as set forth in claim 1, further including a memory element accessible by the electronic control element and configured to store the measurements of the trace gas from the plurality of sensors, and to store information associated with the electronic control element activating the alarm.

17. The system as set forth in claim 1, further including a one or more reservoirs of a test gas and one or more valves associated with the one or more reservoirs, and wherein the electronic control element is configured to test the system by opening the one or more valves and releasing the test gas from the one or more reservoirs for measurement by the plurality of sensors.

18. The system as set forth in claim 17, wherein the test gas comprises the trace gas.

19. The system as set forth in claim 17, wherein the test gas comprises carbon monoxide.

20. A system for detecting a smoldering of a material in a processing equipment, the processing equipment having an air inlet and an air outlet, the system comprising:
a plurality of electro-chemical sensors configured to measure concentrations of carbon monoxide, including a first electro-chemical sensor configured to measure a first concentration of carbon monoxide at the air inlet, and a second electro-chemical sensor configured to measure a second concentration of carbon monoxide at the air outlet;
an electronic control element configured to—
receive the measurements of carbon monoxide simultaneously from the plurality of electro-chemical sensors,
consider the first concentration of carbon monoxide and the second concentration of carbon monoxide simultaneously to determine an amount of carbon monoxide being produced in the processing equipment, wherein the electronic control element takes into account a delay, a dilution, and a time spread of any carbon monoxide moving through the processing equipment between the first electro-chemical sensor and the second electro-chemical sensor,
determine whether the amount of carbon monoxide being produced in the processing equipment exceeds a threshold value indicative of smoldering,
activate an alarm if the amount of carbon monoxide being produced in the processing equipment exceeds the threshold value, and
determine a rate of change of the concentration of carbon monoxide being produced in the processing equipment; and
a user interface configured to allow a user to interact with the electronic control element, including resetting the alarm, viewing current and past measurements of carbon monoxide, and viewing information associated with the electronic control element activating the alarm.

21. A method for detecting a smoldering of a material in a processing equipment, the processing equipment having a first air inlet and an air outlet, the system comprising:
measuring with a plurality of electro-chemical sensors concentrations of carbon monoxide, including measuring a first concentration of carbon monoxide at the first air inlet, and measuring a second concentration of carbon monoxide at the air outlet;
receiving at an electronic control element the measurements of carbon monoxide simultaneously from the plurality of electro-chemical sensors;
considering by the electronic control element the first concentration of carbon monoxide and the second concentration of carbon monoxide simultaneously to determine an amount of carbon monoxide being produced in the processing equipment, including taking into account a delay, a dilution, and a time spread of any carbon monoxide moving through the processing equipment between the first air inlet and the air outlet;
determining by the electronic control element whether the amount of carbon monoxide being produced in the processing equipment exceeds a threshold value indicative of smoldering;
activating by the electronic control element an alarm if the amount of carbon monoxide being produced in the processing equipment exceeds the threshold value; and
facilitating with a user interface a user interacting with the electronic control element, including allowing the user to reset the alarm, view current and past measurements of carbon monoxide, and view information associated with the electronic control element activating the alarm.

22. The method as set forth in claim 21, wherein the material is selected from the group consisting of foods, coals, chemicals, and pharmaceuticals.

23. The method as set forth in claim 21, wherein the processing equipment is selected from the group consisting of: dryers, dust collectors, and a mills.

24. The method as set forth in claim 21, the processing equipment further including a second air inlet, one of the plurality of electro-chemical sensors measuring a third concentration of carbon monoxide at the second air inlet, and wherein the electronic control element further considers the third concentration of carbon monoxide simultaneous with the first and second concentration of carbon monoxide to determine the amount of carbon monoxide being produced in the processing equipment.

25. A system for detecting a smoldering of a material in a processing equipment, the processing equipment having a first air inlet and an air outlet, the system comprising:
a plurality of sensors configured to measure concentrations of a trace gas, including a first sensor configured to measure a first concentration of the trace gas at the first air inlet, and a second sensor configured to measure a second concentration of the trace gas at the air outlet;
an electronic control element configured to receive the measurements of the trace gas simultaneously from the plurality of sensors, consider the first concentration of the trace gas and the second concentration of the trace gas simultaneously to determine an amount of the trace gas being produced in the processing equipment, differentiate between slow variations of the first and second concentrations of the trace gas due to sensor drift and rapid variations of the first and second concentrations of the trace gas due to smoldering, determine whether the amount of the trace gas being produced in the processing equipment exceeds a threshold value indicative of smoldering, and activate an alarm if the amount of the trace gas being produced in the processing equipment exceeds the threshold value; and
a user interface configured to allow a user to interact with the electronic control element, including resetting the alarm.

26. A system for detecting a smoldering of a material in a processing equipment, the processing equipment having a first air inlet and an air outlet, the system comprising:
a plurality of sensors configured to measure concentrations of a trace gas, including a first sensor configured to measure a first concentration of the trace gas at the first air inlet, and a second sensor configured to measure a second concentration of the trace gas at the air outlet;
an electronic control element configured to receive the measurements of the trace gas simultaneously from the plurality of sensors, consider the first concentration of the trace gas and the second concentration of the trace gas simultaneously to determine an amount of the trace gas being produced in the processing equipment, determine whether the amount of the trace gas being produced in the processing equipment exceeds a threshold value indicative of smoldering, wherein the electronic control element considers an equipment profile for the processing equipment, wherein the equipment profile relates the trace gas concentration to a plurality of different air flow rates for the processing equipment, and activate an alarm if the amount of the trace gas being produced in the processing equipment exceeds the threshold value; and a user interface configured to allow a user to interact with the electronic control element, including resetting the alarm.

27. A system for detecting a smoldering of a material in a processing equipment, the processing equipment having a first air inlet and an air outlet, the system comprising:

a plurality of sensors configured to measure concentrations of a trace gas, including a first sensor configured to measure a first concentration of the trace gas at the first air inlet, and a second sensor configured to measure a second concentration of the trace gas at the air outlet;

an electronic control element configured to receive the measurements of the trace gas simultaneously from the plurality of sensors, consider the first concentration of the trace gas and the second concentration of the trace gas simultaneously to determine an amount of the trace gas being produced in the processing equipment, determine whether the amount of the trace gas being produced in the processing equipment exceeds a threshold value indicative of smoldering, wherein the electronic control element considers a smoldering profile for the material, wherein the smoldering profile relates trace gas concentration to time and temperature for the material, and activate an alarm if the amount of the trace gas being produced in the processing equipment exceeds the threshold value; and a user interface configured to allow a user to interact with the electronic control element, including resetting the alarm.

\* \* \* \* \*

UNITED STATES PATENT AND TRADEMARK OFFICE
CERTIFICATE OF CORRECTION

PATENT NO.         : 9,841,400 B2
APPLICATION NO.    : 14/856833
DATED              : December 12, 2017
INVENTOR(S)        : Vingerhoets et al.

It is certified that error appears in the above-identified patent and that said Letters Patent is hereby corrected as shown below:

On the Title Page

Item (75) Inventors should read as follows:
-- Jim Vingerhoets, Rijkevorsel, BE (US);
Jan-Baart SEymortier,
Onez-Lieve-Vrouw-Waver, BE (US);
Gerhardt Jacobsen; Vaerloese, DE (US);
Anders Sehested, Roskilde; DE (US). --

Signed and Sealed this
Tenth Day of July, 2018

Andrei Iancu
*Director of the United States Patent and Trademark Office*